US010179226B2

United States Patent
Kanner et al.

(10) Patent No.: US 10,179,226 B2
(45) Date of Patent: Jan. 15, 2019

(54) PRESSURE LIMITING MECHANISM FOR FLUID DISPLACEMENT AND PRESSURIZING SYRINGE AND METHOD OF ASSEMBLY

(71) Applicant: ATRION MEDICAL PRODUCTS, INC., Arab, AL (US)

(72) Inventors: Rowland W. Kanner, Guntersville, AL (US); Brian A. Roberts, Owens Cross Roads, AL (US)

(73) Assignee: ATRION MEDICAL PRODUCTS, INC., Arab, AL (US)

( * ) Notice: Subject to any disclaimer, the term of this patent is extended or adjusted under 35 U.S.C. 154(b) by 0 days.

(21) Appl. No.: 15/199,049

(22) Filed: Jun. 30, 2016

(65) Prior Publication Data

US 2017/0021144 A1    Jan. 26, 2017

Related U.S. Application Data

(60) Provisional application No. 62/195,167, filed on Jul. 21, 2015.

(51) Int. Cl.
| | |
|---|---|
| *A61M 29/00* | (2006.01) |
| *A61M 25/10* | (2013.01) |
| *A61M 5/31* | (2006.01) |
| *A61M 39/22* | (2006.01) |
| *A61M 5/48* | (2006.01) |

(52) U.S. Cl.
CPC .... *A61M 25/10182* (2013.11); *A61M 5/3134* (2013.01); *A61M 25/10184* (2013.11); *A61M 25/10185* (2013.11); *A61M 39/22* (2013.01); *A61M 5/488* (2013.01)

(58) Field of Classification Search
CPC ...... A61M 25/10182; A61M 25/10185; A61M 25/10184; A61M 39/22; A61M 5/3134; A61M 5/488
See application file for complete search history.

(56) References Cited

U.S. PATENT DOCUMENTS

| | | |
|---|---|---|
| 3,311,422 A | 3/1967 | Oberthur |
| 3,354,638 A | 11/1967 | Kersting |
| 3,450,443 A | 6/1969 | Bueler |

(Continued)

FOREIGN PATENT DOCUMENTS

| | | |
|---|---|---|
| JP | 2012-517860 A | 8/2012 |
| JP | 2013-226193 A | 11/2013 |

*Primary Examiner* — Rebecca E Eisenberg
(74) *Attorney, Agent, or Firm* — Clark Hill PLC; James R. Foley

(57) ABSTRACT

A syringe which has an intended pressure limit. The syringe includes a syringe body, and a pressure-limiting mechanism is disposed inside the syringe body. The pressure-limiting mechanism may comprise a valve body which is spring biased in the syringe body. In one embodiment, the pressure-limiting mechanism is provided in the form the valve assembly having a valve seal which moves into sealing engagement with an internal wall of a valve bore in the syringe housing once the intended pressure limit is reached. In another embodiment, the pressure-limiting mechanism is provided in the form of the valve assembly having a valve seat which moves into sealing or plugged engagement with a valve plug once the intended pressure limit is reached. Regardless of the exact configuration, preferably the syringe is simple, reliable, easy to assembly, and easy to sterilize given its low number of parts.

11 Claims, 6 Drawing Sheets

(56) References Cited

U.S. PATENT DOCUMENTS

| | | |
|---|---|---|
| 3,498,681 A | 3/1970 | Bueler |
| 3,532,390 A | 10/1970 | Bueler |
| 3,597,014 A | 8/1971 | Stokes |
| 3,608,977 A | 9/1971 | Kersting |
| 3,680,921 A | 8/1972 | Falk |
| 3,680,922 A | 8/1972 | Kawai |
| 3,754,792 A | 8/1973 | Ishigami et al. |
| 4,027,923 A | 6/1977 | Saito |
| 5,462,341 A | 10/1995 | Koyano et al. |
| 9,101,739 B2 | 8/2015 | Lesch, Jr. et al. |
| 2010/0211007 A1 | 8/2010 | Lesch, Jr. et al. |

PRESSURE LIMITING MECHANISM FOR FLUID DISPLACEMENT AND PRESSURIZING SYRINGE AND METHOD OF ASSEMBLY

RELATED APPLICATION (PRIORITY CLAIM)

This application claims the benefit of U.S. Provisional Application Ser. No. 62/195,167, filed Jul. 21, 2015, which is hereby incorporated herein by reference in its entirety.

BACKGROUND

The present invention generally relates to pressurizing syringes which are configured to inherently limit the pressure they supply, and methods of assembling such syringes.

In some procedures involving balloon catheters, medical technicians and doctors must carefully monitor both the balloon's effect on the tissue with which the balloon is engaging, as well as the pressure being delivered by the syringe to the balloon. Pressure monitoring during these procedures must be performed in order to avoid harming tissue or damaging the balloon. In these types of applications, for many years, fluid displacement and pressurization syringes equipped with manometers for monitoring delivered pressure have been used to inflate medical balloon catheters, deliver stents and perform discography.

In certain, less critical medical procedures however, catheter balloons need only be expanded to their full pressure and volume capacity, and therapeutic injections simply must not exceed certain pressure limits. For these types of applications, it is possible to use a more simple, limited pressure delivery syringe. Examples of procedures that can be performed with a simple, limited pressure delivery syringe include: Expansion of tear duct passages to treat epiphora, dilation of sinus passages to restore flow, opening eustachian tubes to promote drainage of the inner ear, and injection of stem cells under controlled delivery pressure. For procedures of these types, the added expense of a manometer to monitor pressure is not essential if the delivery pressure can be controlled with a simple and less expensive pressure limiting mechanism.

U.S. Pat. No. 9,101,739 discloses a pressure-limiting syringe primarily for use in the treatment of sinusitis with a balloon catheter. The device disclosed therein relies upon a syringe having a valve body section contained within a separate housing, a spring controlled internal valve spool, an external bypass channel, a bypassing seal gated shutoff port to stop flow, and a bonded on housing (exposed to pressurized operating fluid) that contains the valve body and an axially oriented Luer connector. The device is relatively complex, and includes many parts.

SUMMARY

An object of an embodiment of the present invention is to provide a syringe which has a pressure-limiting mechanism therein, such that the syringe delivers pressure at an intended limit.

Another object of an embodiment of the present invention is to provide a method of assembling such a syringe.

Briefly, an embodiment of the present invention provides a syringe which includes a syringe body. A valve assembly is disposed inside the syringe body. The valve assembly comprises a valve spool which is spring biased in the syringe body. The valve assembly functions to effectively define the intended pressure limit of the syringe.

In one specific embodiment, the valve spool provides a valve seal which engages and seals against an internal wall of the syringe body when the intended pressure limit is reached.

In another specific embodiment, the valve spool comprises a valve seat which engages a valve plug, such as a valve needle, when the intended pressure limit is reached.

Regardless of the exact configuration, preferably the syringe is simple, reliable, easy to assemble, and easy to sterilize given its low number of parts. Preferably, the syringe does not contain sealed off internal dead spaces, rely upon a seal gated shut-off port, require bypass channels external to the syringe body, or include bonded housing junctions exposed to the pressurized operating fluid. Preferably, the syringe provides a side mounted delivery port for convenience in use, but does not have a high number of seals, has only a single internal spring, does not rely upon internal one way valve schemes or closely fitted parts, and does not require a bypass shut-off port. While all this is preferred, the present invention can take many forms, and the claims herein shall define the scope of the claimed invention.

BRIEF DESCRIPTION OF THE DRAWINGS

The organization and manner of the structure and operation of the invention, together with further objects and advantages thereof, may best be understood by reference to the following description taken in connection with the accompanying drawings wherein like reference numerals identify like elements in which.

DESCRIPTION OF ILLUSTRATED EMBODIMENTS

Figure 1:
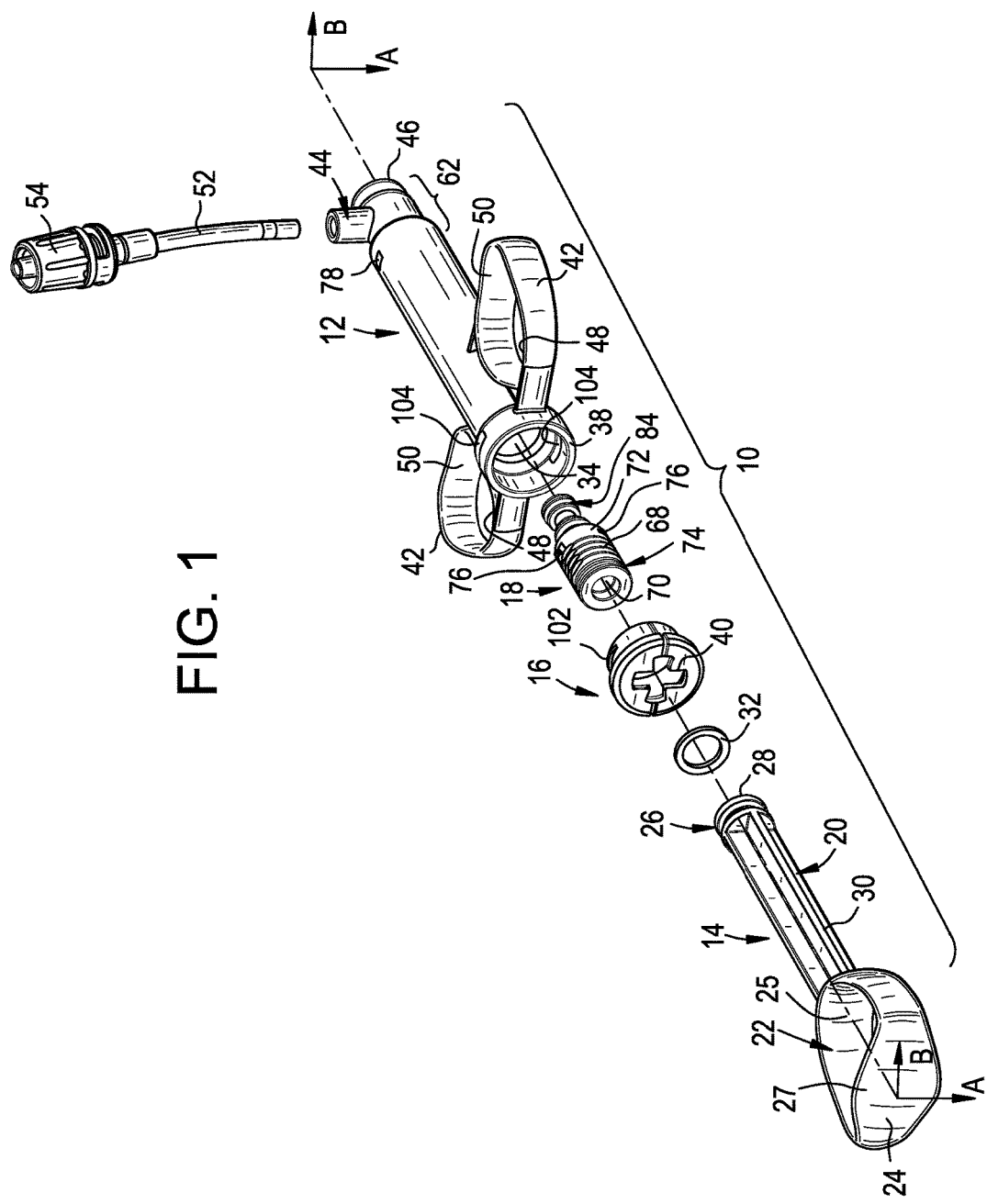
FIG. 1 is an exploded perspective view of a syringe which is in accordance with a first embodiment of the present invention, and showing a Luer connector connected to a delivery hose which is engageable with the syringe.

While this invention may be susceptible to embodiment in different forms, there are shown in the drawings and will be described herein in detail, specific embodiments with the understanding that the present disclosure is to be considered an exemplification of the principles of the invention, and is not intended to limit the invention to that as illustrated.

FIGS. 1-4 illustrate an inflation device or syringe 10 which is in accordance with a first embodiment of the present invention. The syringe 10 is simple, easy to assemble, and comprises very few parts.

The syringe 10 comprises only four main components—a syringe body 12, a plunger 14, a plunger retainer 16, and a valve assembly 18. The plunger 14 can be pushed (i.e., advanced) or pulled (i.e., withdrawn) relative to the syringe body 12 in order to increase or decrease, respectively, the pressure supplied by the syringe 10, while the valve assembly 18 functions to inherently limit the pressure which is supplied by the syringe 10, thereby defining the syringe's intended pressure limit.

As shown in FIG. 1, the plunger 14 may comprise a plunger body 20 having a dual function thumb ring 22 at its proximal end 24 (providing a primary thumb grip 25 and a secondary thumb grip 27), a piston 26 at its distal end 28, an elongated stem 30 disposed between the thumb ring 22 and the piston 26, and a sealing member or plunger piston seal 32 (such as an O-ring) on the piston 26. As shown in FIG. 1, the syringe body 12 has a plunger bore 34 into which the plunger 14 extends, such that the piston 26 is disposed in the plunger bore 34 inside the syringe body 12 (see FIGS. 2 and 4). The plunger piston seal 32 engages an internal wall 36 inside the syringe body 12, thereby sealing the plunger bore 34 inside the syringe body 12.

The plunger retainer 16 is engaged with the syringe body 12, at an end 38 of the syringe body 12, for limiting or prohibiting rotation of the plunger 14 relative to the syringe body 12. Alternatively, the plunger retainer 16 can be formed as being integral with the syringe body 12. As shown in FIG. 1, the plunger retainer 16 may comprise two parts which snap into the end 38 of the syringe body 12, and effectively mate together to provide at least one anti-rotation boss 40 which corresponds (i.e., keys) to the shape of the stem 30 of the plunger 14, thereby limiting or preventing the plunger 14 from completely rotating relative to the syringe body 12, and further prohibiting the piston 26 from being readily withdrawn fully out of the syringe body 12.

The syringe body 12 is preferably a single molded piece, having an opposed pair of finger rings 42 (see FIGS. 1 and 2) proximate the end 38 of the syringe body 12 for user interaction with the syringe 10, and a socket 44 (see FIGS. 1, 3 and 4) proximate an opposite end 46 of the syringe body 12. The finger rings 42 preferably comprise dual function finger rings having both a primary finger grip 48 and a secondary finger grip 50 for user interaction. The socket 44 is configured to engage structure such as a delivery hose 52 (see FIGS. 1, 3 and 4) which may be connected to a Luer connector 54, as shown in FIGS. 1 and 4, so the syringe 10 can ultimately supply pressure to a device such as a balloon catheter via the socket 44. While a delivery hose 52 and/or Luer connector 54 are shown in FIGS. 1, 3 and 4, the socket 44 may very well be connected to different types of structure.

Figure 2:
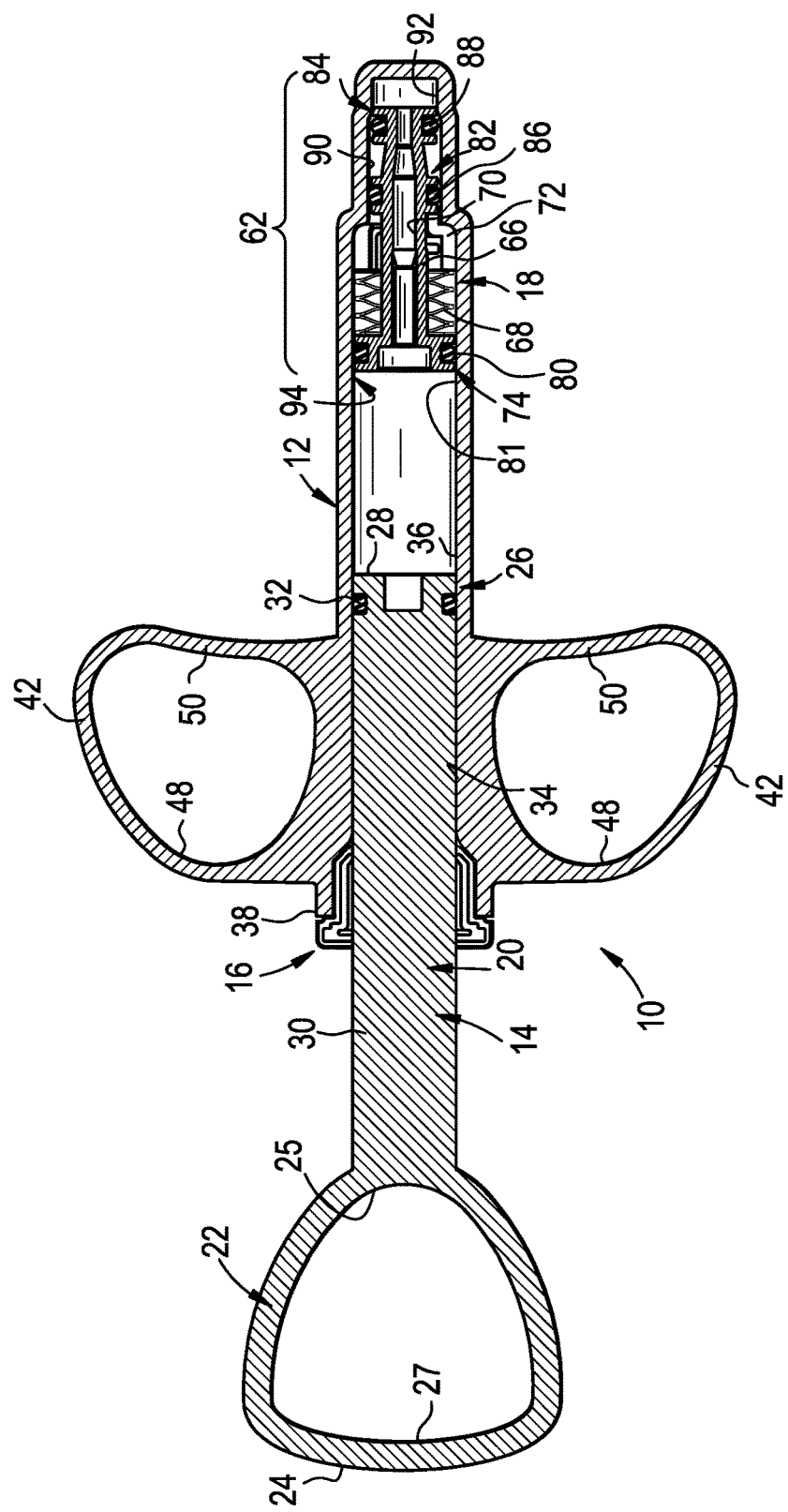
FIG. 2 is a cross-sectional view of the syringe shown in FIG. 1, taken along line A-A of FIG. 1, showing the syringe before an intended pressure limit is reached.
Figure 3:
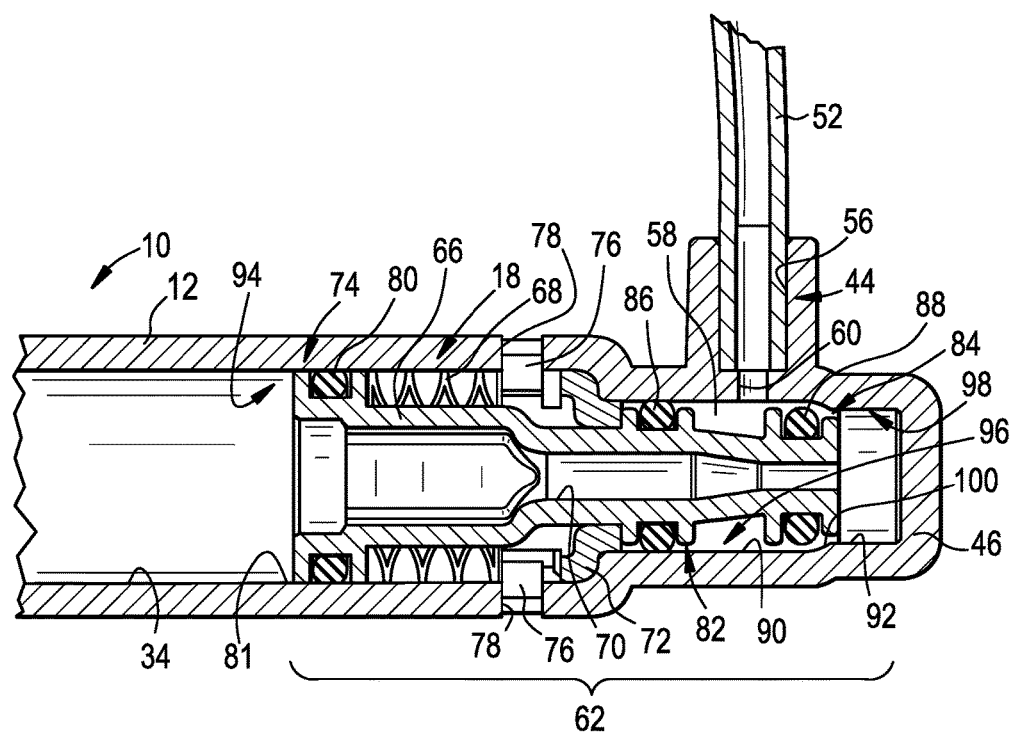
FIG. 3 is a cross-sectional view of a portion of the syringe shown in FIG. 1, taken along line B-B of FIG. 1, showing the syringe before an intended pressure limit is reached, and showing the delivery hose engaged with the syringe.
Figure 4:
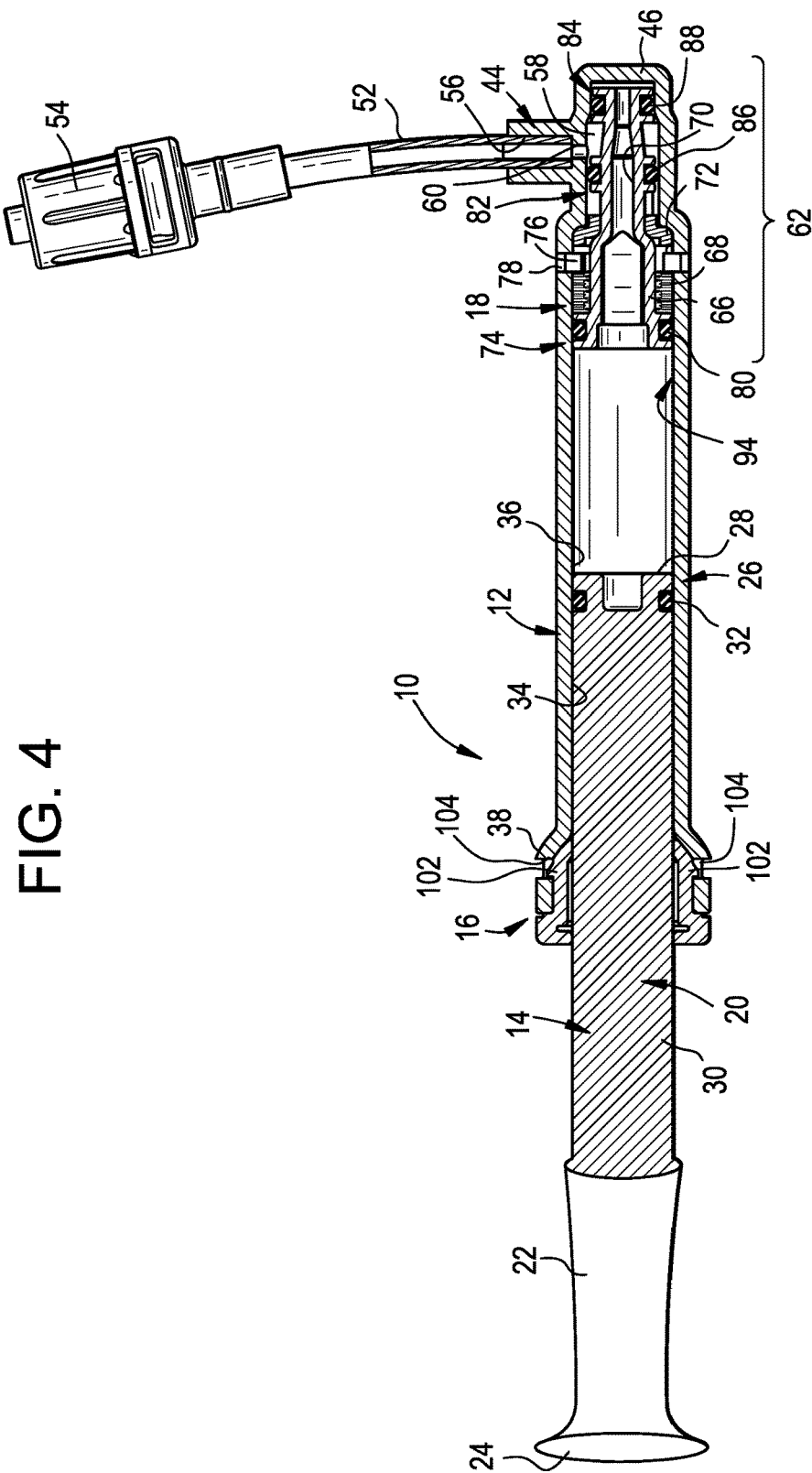
FIG. 4 is a cross-sectional view of the syringe shown in FIG. 1, taken along line B-B of FIG. 1, showing the syringe after the intended pressure limit is reached, and showing the Luer connector connected to the delivery hose which is engaged with the syringe.

Regardless, the socket 44 preferably includes an opening 56 which is in fluid communication with a pressure chamber 58 inside the syringe body 12, such as via a side mounted delivery port 60 as shown in FIGS. 3 and 4. As shown in FIGS. 2 and 4, the piston 26 of the plunger 14 is disposed in the plunger bore 34, and can be moved back and forth therein using the thumb ring 22 of the plunger 14 (in conjunction with the finger rings 42 on the syringe body 12), thereby changing the pressure which is supplied by the syringe 10 (via the pressure chamber 58 and socket 44).

The syringe body 12 includes a valve section 62 in which the valve assembly 18 is disposed. A preferred embodiment of the valve assembly 18 will now be described. Preferably, the valve assembly 18 comprises a valve spool 66 which is spring biased in the syringe body 12 via compression spring 68. The valve spool 66 has a central throughbore 70 which defines a fluid passageway from one end of the valve spool 66 to the other, through which fluid can flow between the plunger bore 34 and the pressure chamber 58 (so long as the intended pressure limit has not been reached).

The spring 68 is preferably disposed between a spring perch 72 and a valve piston 74 which is provided on the valve spool 66. As shown in FIGS. 1, 3 and 4, preferably the spring perch 72 is engaged with the syringe body 12 via spring perch retainer lugs 76 which engage corresponding spring perch retainer lug notches 78 provided on the syringe body 12. Of course, other means may be used to retain the spring perch 72 relative to the syringe body 12.

Preferably, the valve piston 74 has a valve seal 80 (such as an O-ring) disposed thereon which contactably engages internal wall 81 of the syringe body 12. Preferably, there are one or more additional valve pistons 82, 84 provided on the valve spool 66, and each of the valve pistons 82, 84 also has a corresponding valve seal 86, 88 (such as an O-ring) disposed thereon which contactably engages a corresponding internal wall 90, 92 of the syringe body 12.

Preferably, each valve piston 74, 82, 84 of the valve spool 66 is sized differently relative to each other. Specifically, the valve spool 66 may comprise a first valve piston 74, a second valve piston 82, and a third valve piston 84, wherein the first valve piston 74 is the largest (i.e., has the largest diameter), the third valve piston 84 is the smallest (i.e., has the smallest diameter), and the second valve piston 82 is sized between the first valve piston 74 and the third valve piston 84 (i.e., has a diameter which is smaller than that of the first valve piston 74, but is larger than that of the third valve piston 84).

Preferably, the inner profile of the syringe body 12 is such that the syringe body 12 has a plurality of valve bores 94, 96, 98, each having a different inside diameter. Specifically, the syringe body 12 may have a first valve bore 94 having an inside diameter which is defined by internal wall 81 which is engaged by the first valve piston 74 of the valve spool 66, a second valve bore 96 having an inside diameter which is defined by internal wall 90 which is engaged by the second valve piston 82 of the valve spool 66, and a third valve bore 98 having an inside diameter which is defined by internal wall 92 which is engaged by the third valve piston 84 of the valve spool 66. Preferably, an entrance cone 100 is provided leading into the third valve bore 98 for guiding the third valve piston 84 into the third valve bore 98.

While the first valve piston 74 and the second valve piston 82 preferably continuously engage and contact corresponding internal walls 81 and 90, respectively, in the syringe body 12, the third valve piston 84 is preferably disengaged from internal wall 92, but is engageable therewith should the internal pressure in the syringe 12 reach its intended pressure limit. Specifically, in operation, as the plunger 14 is pushed into the syringe body 12, pressure in the syringe 10 increases. As internal pressure in the syringe 10 increases, the valve spool 66 is pushed forward in the syringe body 12, against the force of the spring 68. At some point, should the internal pressure in the syringe 10 increase sufficiently such that it reaches its intended pressure limit, the valve spool 66 becomes pushed sufficiently forward against the spring 68 such that the third valve piston 84 enters the third valve bore 98 and engages internal wall 92.

FIGS. 2 and 3 show the state of the syringe 10 wherein its intended pressure limit has not yet been reached, and the third valve piston 84 has not yet entered the third valve bore 98. FIG. 4 shows the state of the syringe 10 wherein its intended pressure limit has been reached (i.e., by pushing the plunger 14 sufficiently into the syringe body 12), and the third valve piston 84 has entered the third valve bore 98 causing the valve seal 88 thereon to seal against the internal wall 92 in the third valve bore 98. This seal 88 prevents fluid from inside the valve spool 66 from traveling to the pressure chamber 58, and vise-versa. As such, the pressure at the socket 44 is maintained and does not increase, even if the plunger 14 is pushed more fully into the syringe body 12.

Assembling the syringe 10 is quite easy, as assembly is accomplished merely through insertion and/or snapping the mating parts together. First, the valve assembly 18 is inserted into the plunger bore 34 of the syringe body 12, down into the valve section 62 of the syringe body 12, such that the first valve seal 80 of the valve spool 66 seals against the internal wall 81 in the first valve bore 94, the second valve seal 86 of the valve spool 66 seals against the internal wall 90 in the second valve bore 96, and the third valve seal 88 of the valve spool 66 resides within the pressure chamber 58 within the syringe body 12. As shown in FIG. 4, the valve assembly 18 is retained within the syringe body 12 by the spring perch 72, via the spring perch retainer lugs 76 which engage the corresponding spring perch retainer lug notches 78 on the syringe body 12, provided proximate the bottom of first valve bore 94. It should be understood however, that although first valve bore 94 as shown herein is illustrated to be of the same diameter as plunger bore 34, the plunger bore of any syringe utilizing this valve concept may be made equal or larger than the syringe's first valve bore without deviating from the spirit of the invention.

After the valve assembly 18 has been installed within the valve section 62 of the syringe body 12, the piston 26 of the plunger 14 is then inserted into the plunger bore 34 where it is then retained therein by insertion of the plunger retainer 16 as best shown in the section view shown in FIG. 4. The plunger retainer 16 may be retained by the syringe body 12 via plunger retainer lugs 102 on the two parts of the plunger retainer 16, which snap into corresponding notches 104 on the syringe body 12, thereby securing the plunger retainer 16 to the syringe 10 and retaining the piston 26 inside the syringe body 12. At least one anti-rotation boss 40 which is provided by the plunger retainer 16 preferably limits rotation of the plunger 14 to an amount suitable for comfortable alignment with a user's thumb or palm but sufficient to prevent its full rotation if the syringe 10 is grasped only by the dual function thumb ring 22.

With regard to operation, inflation syringes for use with balloon catheters are generally filled with either sterile injectable normal saline solution or a mix of injectable normal saline and radio-opaque contrast media. When used for controlled injection purposes, the syringe may be filled with either a water based or water soluble medicament or stem cell mixture, for example. Although water based solutions are most commonly delivered, any solution or mixture could be delivered with the syringe as long as it is liquid in nature and contains no materials in solid or granular form, since the solution to be delivered by the syringe must serve as the essential working fluid of its hydraulically operated pressure limiting valve.

Filling the syringe 10 with solution involves drawing the liquid up through the Luer connector 54 and into the syringe body 12 by withdrawing the plunger 14 from a fully distal to a fully proximal position. Gripping the syringe 10 is most easily accomplished by placing ones adjacent fingers into the dual function finger rings 42 (shown in FIG. 2), against the primary finger grips 48 and placing the thumb into thumb ring 22. Expanding the hand from this gripping position moves plunger 14 distally, and thereby allows fluid to be drawn through Luer connector 54 and delivery port 60 into and through the fluid passageway 70 provided in the valve spool 66, and finally into plunger bore 34. Once the syringe 10 has been fully charged with fluid and the desired fluid capacity set for delivery, it is then ready for connection and use with a balloon catheter or injection needle.

Depending upon the plunger's position at the start of a delivery procedure, thumb ring 22 and the dual function finger rings 42 are designed to accommodate most users hands by allowing the syringe 10 to be grasped in any of four different ways, whichever is most comfortable for the user and whichever allows the user to most effectively apply hand pressure for fluid delivery. Plunger 14 can be operated with a thumb placed inside thumb ring 22 against the primary thumb grip 25 or users can place the palm of their hand against the secondary thumb grip 27 in order to apply more force with the palm of their hand. Similarly, the dual function finger rings 42 can receive adjacent fingers within the ring against the primary finger grip 48 or they may be grasped by the secondary finger grip 50 if a user feels the need to spread their hand out more to applying force against the plunger 14. A user can therefore move plunger 14 distally for pressurization and dispensing by using whichever gripping method they find to be most comfortable and advantageous.

Activation of the pressure limiting mechanism (i.e., valve assembly 18) and control of both fluid pressure and flow results from system pressure acting upon the three valve pistons 74, 82, 84 of the valve spool 66, and the resulting compressive force delivered to spring 68. A balloon catheter coupled to Luer connector 54, for instance, can be expanded by advancing plunger 14 distally to cause fluid to flow from plunger bore 34, through fluid passageway 70 of valve spool 66, into pressure chamber 58 and out delivery port 60 to Luer connector 54 where it can enter a balloon catheter's connector. Pressure created within the system by user force against plunger 14 is transmitted along the same path as fluid flow and it pushes against both the first valve piston 74 and the second valve piston 82. Because the effective area of second valve piston 82 is slightly smaller than the effective area of first valve piston 74, and due to its placement in the second valve bore 96 where it receives pressure from the pressure chamber side, the force delivered to valve spool 66 by the second valve piston 82 in response to pressure from plunger 14 opposes the force from the first valve piston 74, but with slightly less force due to the difference in effective area between these two pistons 74 and 82. The excess energy generated by first valve piston 74 is absorbed by spring 68, and the spring 68 responds by compressing which in turn allows valve spool 66 to traverse distally within valve section 62 of the syringe body 12.

When a catheter balloon, for example attached to Luer connector 54, begins to resist expansion and pressure therefore builds within the syringe 10, valve spool 66 further compresses spring 68 and moves distally as the valve's intended pressure limit is approached. Immediately before reaching the intended pressure limit of the valve assembly 18, spring 68 will have become compressed sufficiently to allow the third valve seal 88 to proximate the entrance cone 100 at the open end of the third valve bore 98 and begin restricting the communication of pressurized fluid in fluid passageway 70 with pressure chamber 58, delivery port 60 and subsequently, for example, the balloon catheter attached to Luer connector 54. The benefit of this valve's construction whereby a slightly smaller second valve piston 82 opposes the driving first valve piston 74 is that the resulting force between both pistons can, by design, be made to be very small compared to the force first valve piston 74 alone would exert under operating pressure. With this small resulting force on hand, actuation of the valve mechanism 18 can therefore be controlled with a small, lightweight, inexpensive spring 68 instead of requiring a large heavy spring. This relationship between the first valve piston 74 ("fvp"), the second valve piston 82 ("svp"), and spring 68 is expressed in the following equation:

$$(\text{Effective Area}_{(fvp)} - \text{Effective Area}_{(svp)}) \times \text{Plunger Bore Pressure} = \text{Force against spring}$$

When valve spool 66 advances distally in response to increased pressure within the system, fluid flow through fluid passageway 70 subsides as firm contact between the third piston seal 88 and entrance cone 100 leads to the engagement of third valve piston 84 with internal wall 92 in the third valve bore 98. Significant movement of plunger 14 is inhibited upon engagement of the third valve piston 84 within the third valve bore 98, as pressure chamber 58 becomes hydraulically blocked against communication with fluid passageway 70 until user force upon plunger 14 is released. Additional distal movement of the plunger 14 serves only to drive valve spool 66 distally to the bottom of the third valve bore 98 which hydraulically prevents any further distal movement of plunger 14. Users sensing this immediate rise in resistance against movement of plunger 14 will therefore receive tactile feedback that the intended pressure limit of the system has been reached. Additionally, upon engagement of the third valve piston 84 within the third valve bore 98 and cessation of flow to pressure chamber 58, residual pressure within pressure chamber 58 is only maintained by down-stream pressure through delivery port 60 by means of, for instance, pressure from the fully inflated balloon catheter attached to Luer connector 54. This pressure bears directly against the effective areas of second valve piston 82 and the effective area of third valve piston 84, and is not relieved until user force against plunger 14 is released. Once user force against plunger 14 has been released, the stored energy of compressed spring 68, momentarily assisted by excess force created by residual pressure against the valve piston 84 sealing off the pressure chamber 58, begins to return the valve spool 66 toward the plunger bore 34. As pressure within the system decreases, valve spool 66 moves toward its original non-pressure position. The relationship between the second valve piston 82 ("svp"), the third valve piston 84 ("tvp") and spring 68 is expressed in the following equation:

$$(\text{Effective Area}_{(svp)} - \text{Effective Area}_{(tvp)}) \times \text{Pressure in Pressure Chamber} = \text{Excess Force}$$

Figure 5:
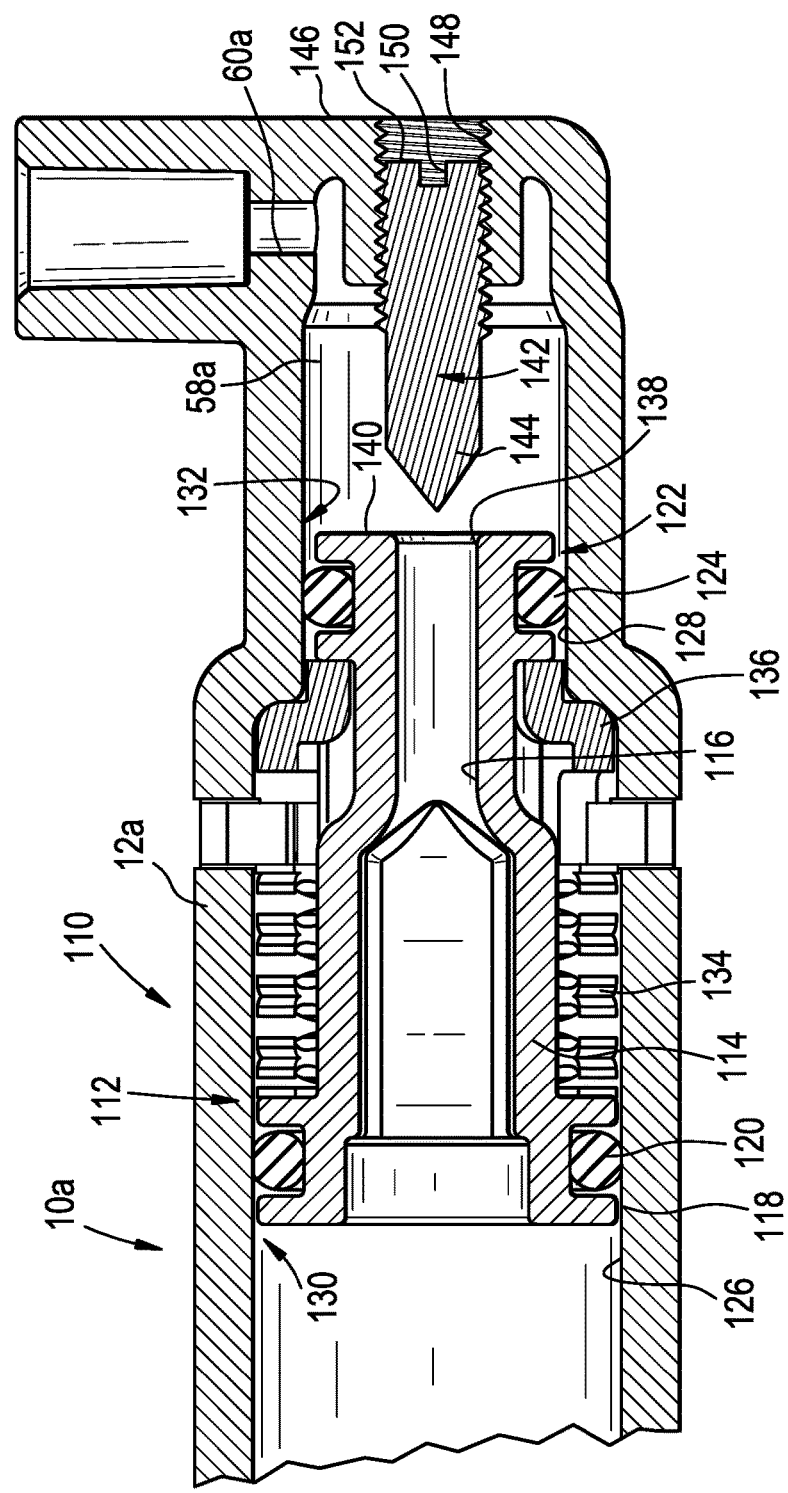
FIG. 5 is a view similar to FIG. 2, but shows an alternative embodiment of the valve mechanism, before an intended pressure limit is reached.
Figure 6:
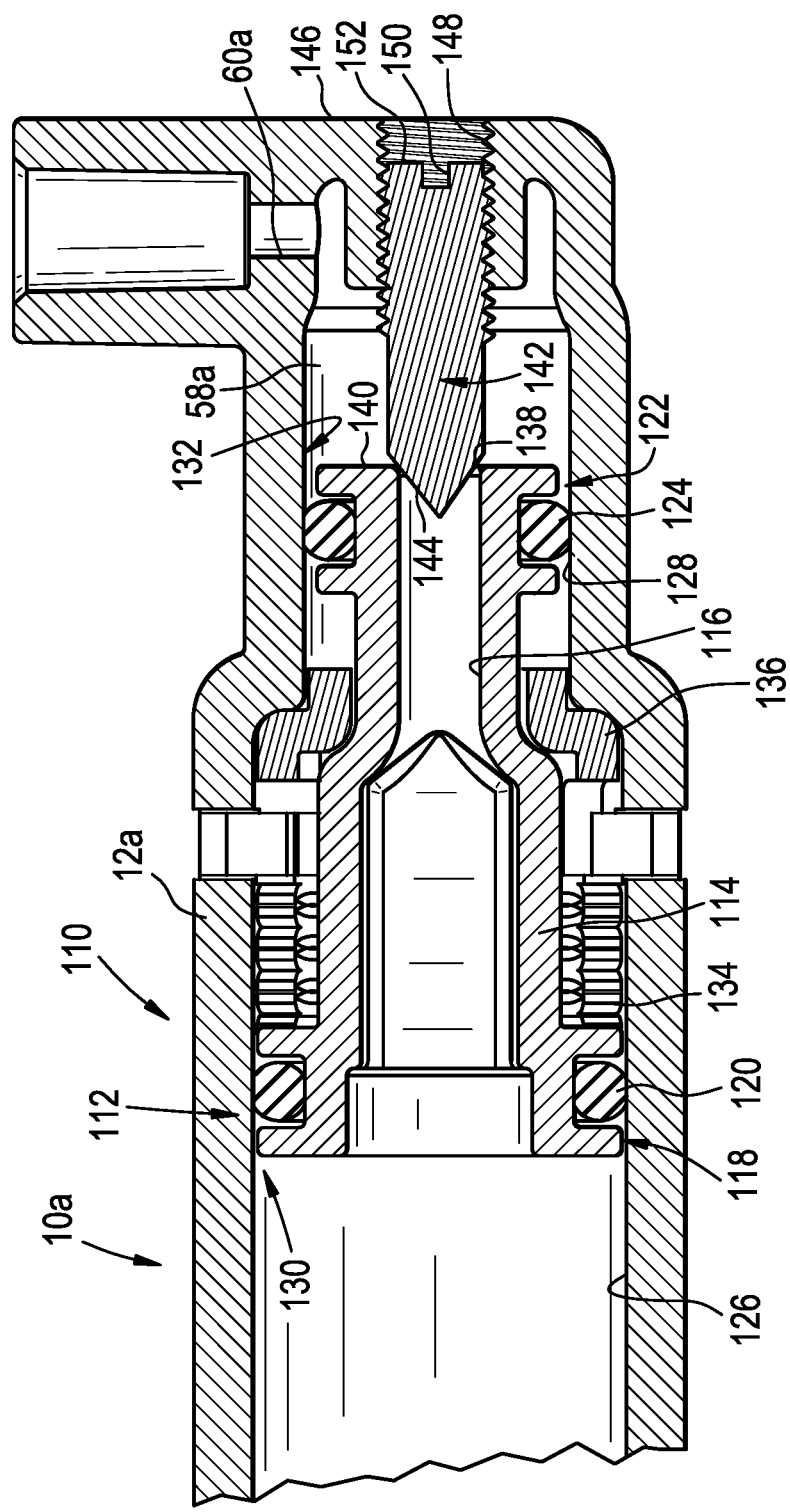
FIG. 6 is a view similar to FIG. 5, but shows the valve mechanism after the intended pressure limit is reached.

FIGS. 5 and 6 illustrate a valve mechanism 110 which is in accordance with an alternative embodiment of the present invention. The valve mechanism 110 can be used in association with a syringe 10a very much like the syringe 10 which was previously described. The valve mechanism 110 includes a valve assembly 112 having a valve spool 114 having a fluid passageway 116 therethrough, thereby providing fluid flow from one end of the valve spool 114 to the other. The valve spool 114 has a first valve piston 118, with valve seal 120, and a second valve piston 122, with valve seal 124. The first valve piston 118 has a larger diameter than the second valve piston 122. Each valve piston 118, 122 is continuously in sealing contact with corresponding internal walls 126, 128 of corresponding valve bores 130, 132 in the syringe body 12a. A compression spring 134 is disposed between the first valve piston 118 and a spring perch 136 which is engaged with the syringe body 12a (in the same way spring perch 72 is engaged with syringe body 12).

Instead of relying upon a third valve piston 84 and an internal wall 92 of a third valve bore 98 to control flow and pressure, the valve mechanism 110 provides that the function of these items are replaced by a valve seat 138 on the distal end 140 of the valve spool 114 and a valve plug 142, such as a valve needle 144, which is disposed at the end 146 of the syringe body 12a, specifically engaged in a threaded bore or mounting 148 at the end 146 of the syringe body 12a.

As shown in FIG. 6, when the valve assembly 112 reaches the intended design pressure and the spring 134 is sufficiently compressed, flow through fluid passageway 116 of the valve spool 114 becomes blocked as a result of the valve seat 138 coming into contact with, and being plugged by, the valve needle 144. Preferably, the valve needle 144 can be adjusted to thereby adjust the intended pressure limit of the syringe 10a. Specifically, preferably the height of the valve needle 144 can be adjusted for calibration, or to change the shut-off pressure of the valve assembly 112, by advancing or withdrawing the valve needle 144 by rotation within the threaded mounting 148. To facilitate this, a notch 150 or other profile can be provided on the end 152 of the valve plug 142 for engagement by an appropriate tool. Residual pressure within pressure chamber 58a received through delivery port 60a (and Luer connector 54, such as is shown in FIGS. 1 and 4) bears against the effective area of the second valve piston 122 which is reduced by the effective area of the contact periphery of the valve seat 138 on valve spool 114 against the valve needle 144.

As such, the first embodiment disclosed herein provides a pressure-limiting mechanism in the form of a valve assembly 18 having a valve seal 88 which moves into sealing engagement with an internal wall 92 of a valve bore 98 once the intended pressure limit is reached. The second embodiment disclosed herein provides a pressure-limiting mechanism in the form of a valve assembly 112 having a valve seat 138 which moves into sealing or plugged engagement with a valve plug 142 once the intended pressure limit is reached.

While two different pressure-limiting mechanisms are disclosed herein, still other variations are possible while staying within the scope of the present invention.

Regardless of which pressure-limiting mechanism is employed, preferably the resulting syringe has an intended pressure limit, has few parts, is easy to assemble, and is easy to sterilize.

While specific embodiments of the invention have been shown and described, it is envisioned that those skilled in the art may devise various modifications without departing from the spirit and scope of the present invention.

What is claimed is:

1. An inflation device configured to pressurize a medical device, said inflation device comprising: a syringe body; a plunger; a valve assembly disposed inside the syringe body and configured to define a pressure limit of the inflation device, wherein the valve assembly comprises a valve spool, wherein the valve spool comprises a first valve piston having an effective area and a second valve piston having an effective area, wherein the effective area of the second valve piston is smaller than the effective area of the first valve piston, further comprising a compression spring disposed between the first valve piston and the second valve piston, wherein a force delivered to the valve spool by the second valve piston in response to pressure from the plunger opposes a force from the first valve piston, wherein excess energy generated by the first valve piston is absorbed by the compression spring and the compression spring responds by compressing which in turn causes the valve spool to traverse distally within the syringe body.

2. An inflation device as recited in claim 1, wherein an inner profile of the syringe body is configured to provide a plurality of valve bores, each valve bore having a different inside diameter.

3. An inflation device as recited in claim 2, wherein the valve spool has a central throughbore which defines a fluid passageway through which fluid flows so long as the intended pressure limit of the inflation device has not been reached.

4. An inflation device as recited in claim 1, wherein the valve spool comprises a third valve piston which seals with an internal wall of the syringe body upon the pressure limit of the inflation device being reached, after at least some compression of the compression spring.

5. An inflation device as recited in claim 1, wherein the valve spool comprises a third valve piston, wherein each valve piston has a valve seal which contactably engages a corresponding internal wall of the syringe body, wherein each valve piston of the valve spool is sized differently relative to each other, wherein the first valve bore has an inside diameter which is defined by an internal wall which is engaged by the first valve piston of the valve spool, wherein the second valve bore has an inside diameter which is defined by an internal wall which is engaged by the second valve piston of the valve spool, and wherein the third valve bore has an inside diameter which is defined by an internal wall which is engaged by the third valve piston of the valve spool.

6. An inflation device as recited in claim 5, wherein the first valve piston and the second valve piston are configured to continuously engage and contact corresponding internal walls of the syringe body, wherein the third valve piston is configured to be disengaged from the internal wall of the syringe body, but is configured to engage the internal wall when the internal pressure in the inflation device reaches its delivered pressure limit.

7. An inflation device as recited in claim 6, further comprising an entrance cone leading into the third valve bore and configured to guide the third valve piston into the third valve bore.

8. An inflation device as recited in claim 1, wherein the valve spool comprises a plurality of valve pistons, wherein each of the valve pistons has a corresponding valve seal, wherein at least one of the valve pistons is configured to continuously engage and contact a corresponding internal wall of the syringe body, wherein at least one of the valve pistons is configured to be disengaged from an internal wall of the syringe body, but is configured to engage the internal wall when the internal pressure in the inflation device reaches its delivered pressure limit.

9. An inflation device as recited in claim 1, wherein the valve spool has a fluid passageway through which fluid flows so long as the intended pressure limit of the inflation device has not been reached, further comprising a valve plug in the inflation device which engages the valve spool when the internal pressure in the inflation device reaches its intended pressure limit, thereby preventing fluid flow out the fluid passageway in the valve spool.

10. An inflation device as recited in claim 1, wherein the syringe body has an internal wall, further comprising a plunger having a plunger piston seal which seals with the internal wall, and further comprising a plunger retainer which is configured to engage the plunger and prohibit substantial rotation of the plunger relative to the syringe body, wherein the syringe body comprises an end, wherein the plunger comprises a stem, wherein the plunger retainer comprises a plurality of parts which snap into the end of the syringe body, wherein the plurality of parts mate together to provide at least one anti-rotation boss which corresponds to a shape of the stem of the plunger, thereby preventing the plunger from completely rotating relative to the syringe body, and further prohibiting the piston from being readily withdrawn fully out of the syringe body.

11. An inflation device as recited in claim 1, wherein the compression spring is disposed between a spring perch which is provided in the syringe body and the valve piston which is provided on the valve spool, wherein the spring perch is engaged with the syringe body via spring perch retainer lugs which engage corresponding spring perch retainer lug notches provided on the syringe body, wherein the valve piston has a valve seal disposed thereon which contactably engages an internal wall of the syringe body.

* * * * *